United States Patent
Wagatsuma

(10) Patent No.: US 9,148,566 B2
(45) Date of Patent: Sep. 29, 2015

(54) X-RAY PHOTOGRAPHIC DEVICE, IMAGE PROCESSING METHOD THEREOF, AND PROGRAM

(75) Inventor: Takanori Wagatsuma, Tokyo (JP)

(73) Assignee: The Yoshida Dental Mfg., Co., Ltd., Sumida-ku, Tokyo (JP)

(*) Notice: Subject to any disclaimer, the term of this patent is extended or adjusted under 35 U.S.C. 154(b) by 415 days.

(21) Appl. No.: 13/824,954

(22) PCT Filed: Sep. 21, 2010

(86) PCT No.: PCT/JP2010/066331
§ 371 (c)(1),
(2), (4) Date: Mar. 18, 2013

(87) PCT Pub. No.: WO2012/039023
PCT Pub. Date: Mar. 29, 2012

(65) Prior Publication Data
US 2013/0188009 A1      Jul. 25, 2013

(51) Int. Cl.
H04N 5/232 (2006.01)
A61B 6/14 (2006.01)
A61B 6/02 (2006.01)
A61B 6/03 (2006.01)
A61B 6/00 (2006.01)

(52) U.S. Cl.
CPC ............ *H04N 5/23238* (2013.01); *A61B 6/025* (2013.01); *A61B 6/032* (2013.01); *A61B 6/14* (2013.01); *A61B 6/5223* (2013.01)

(58) Field of Classification Search
CPC ................................................. H04N 5/23238
USPC ........................................................ 348/36
See application file for complete search history.

(56) References Cited

U.S. PATENT DOCUMENTS 5,600,699 A *  2/1997  Suzuki et al. .................. 378/38
2009/0052617 A1*  2/2009  Sadakane et al. ............... 378/38

FOREIGN PATENT DOCUMENTS

| JP | 7308314 | 11/1995 |
| JP | 8-215191 | 8/1996 |
| JP | 2824602 | 11/1998 |
| JP | 2007-117432 | 5/2007 |
| JP | 2008-229322 | 10/2008 |
| WO | WO 2008/072821 | 6/2008 |

OTHER PUBLICATIONS

International Search Report for International Application No. PCT/JP2012/06631 mailed Jan. 11, 2011.

* cited by examiner

*Primary Examiner* — Christopher S Kelley
*Assistant Examiner* — Jonathan Messmore
(74) *Attorney, Agent, or Firm* — Merchant & Gould P.C.

(57) ABSTRACT

Conventional X-ray photographing has several problems for eliminating the influence from the cervical vertebrae such as rework of original images, causing possible loss of useful information, as well as long processing time and the need for a plurality of panoramic images. The X-ray photographic device according to the present invention can eliminate the influence from the cervical vertebrae projected at around the anterior teeth of the panoramic image of a tooth row, without missing the original image information and without influence of different shapes of cervical vertebrae and X-ray permeability by each subject. In addition, as the present invention achieves these through arithmetic processing, there is no need to intensify X-ray output in the section corresponding to the anterior teeth, nor decelerate the rotating speed of arms during photographing, and it is possible to suppress the X-ray dose received by the subject.

9 Claims, 9 Drawing Sheets

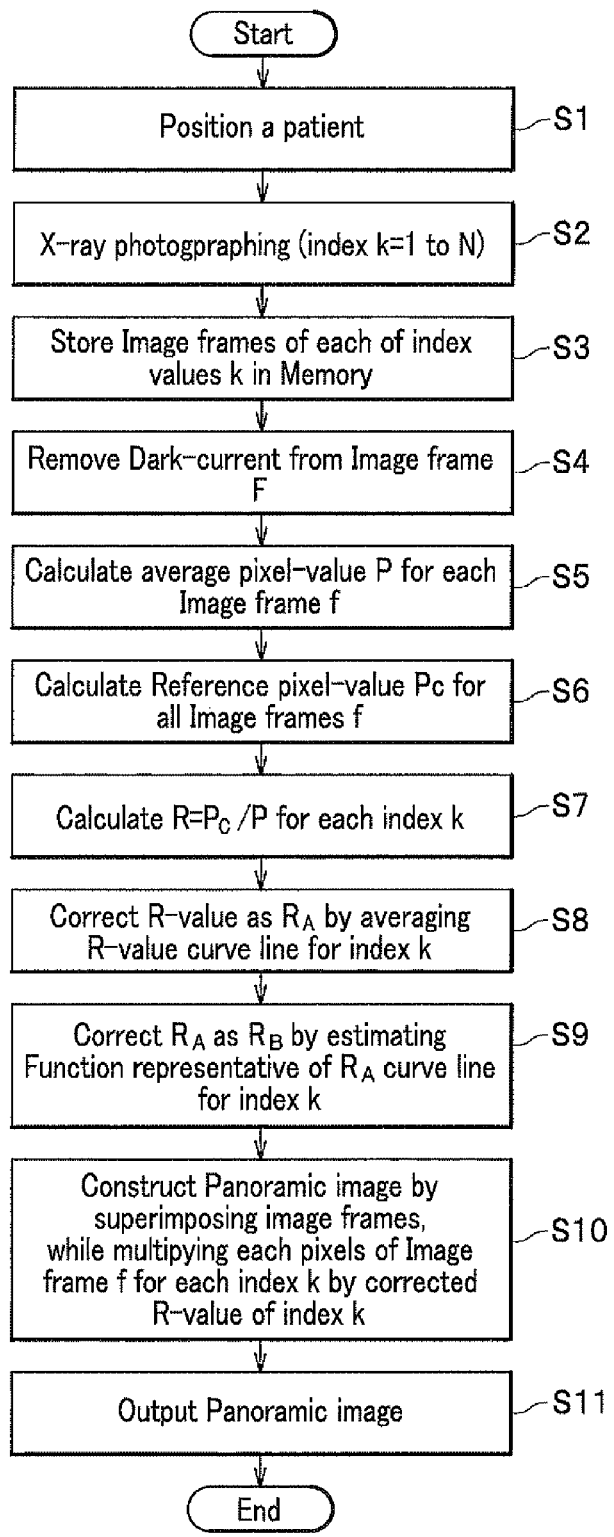

X-RAY PHOTOGRAPHIC DEVICE, IMAGE PROCESSING METHOD THEREOF, AND PROGRAM

This application is a National Stage Application of PCT/JP2010/066331, filed 21 Sep. 2010, which application is incorporated herein by reference. To the extent appropriate, a claim of priority is made to the above disclosed application.

TECHNICAL FIELD

The present invention relates to a technology of an X-ray photographic device, especially to improve the quality of panoramic images by image processing.

BACKGROUND OF THE INVENTION

In general, when a panoramic image of the tooth row is taken with a dental X-ray photographic device, cervical vertebrae appear in the place of the anterior teeth of the panoramic image, making that part white.

Therefore, conventionally, a technique is known to intensify an X-ray output only when photographing the anterior teeth, for ensuring enough X-ray incidents on the image-receiving surface of the X-ray detector. This technique can be classified into two methods. The first method is to intensify the X-ray output uniformly in the section corresponding to the anterior teeth by a predetermined value. The second method is to continuously monitor X-ray incidents on the image-receiving surface of the X-ray detector during photographing and controlling the X-ray output so that X-ray incidents are kept with a predetermined value at all times. It is impossible with the first method to react to different shapes of cervical vertebrae and X-ray permeability by each subject, but with the second method, it is possible to react thereto. However, it is necessary to increase the X-ray dose received by the subject with either one of the methods and that is not preferable.

On the other hand, for example, X-ray photographic devices disclosed in Patent Document 1 and Patent Document 2 construct a panoramic image in which the influence of the cervical vertebrae is eliminated by performing arithmetic processing on the image acquired by X-ray photographing. Hereinafter, an example of eliminating the influence of the cervical vertebrae by a conventional X-ray photographic device will be described, with reference to FIG. 11. FIG. 11 shows a mandibular tooth row 901 and a cervical vertebra 902, as an example. In addition, an imaging plane to construct a panoramic image of the tooth row is indicated by reference numeral 903. Here, each of reference numerals 905 and 906 shows an example of an incident X-ray beam from a predetermined direction to the tooth row 901. Further, an imaging plane to construct a panoramic image of the cervical vertebrae is indicated by reference numeral 904, in order to eliminate the influence of the cervical vertebrae from the panoramic image of a tooth row. The imaging plane 904 sections through the cervical vertebra 902 and the right and left mandibular angles 908. Further, reference numeral 907 indicates a trajectory of the pivot arms arranged with a X-ray generator and a X-ray detector, respectively, at the X-ray photographic device, facing each other and having the tooth row 901 in-between.

The conventional X-ray photographic device first detects the X-rays transmitted through the tooth row 901 by frames and overlays a sequence of image frames to form a panoramic image I1 of the tooth row on the imaging plane 903. Next, the conventional X-ray photographic device forms a panoramic image I2 of the cervical vertebrae on the imaging plane 904. Then, the conventional X-ray photographic device simulates on a computer how the panoramic image I2 of the cervical vertebrae is blurred when it is projected onto the imaging plane 903, to acquire a panoramic image I3 projecting the cervical vertebrae. The conventional X-ray photographic device subtracts the panoramic image I3 projecting the cervical vertebrae from the panoramic image I1 of the tooth row obtained above, to acquire a panoramic image I4 of the tooth row without the influence of the cervical vertebrae.

PRIOR ART DOCUMENTS

Patent Documents

Patent Document 1: Japanese Laid-Open Patent Application No. H07-308314
Patent Document 2: Japanese Patent No. 2824602

SUMMARY OF THE INVENTION

Description of the Related Art

However, according to the conventional X-ray photographic device, an original panoramic image of the imaging plane of the tooth row is reworked significantly during construction, by utilizing a panoramic image of an imaging plane of other than the tooth row. For this reason, there is a possibility that pieces of meaningful information in the original panoramic image might be also eliminated from the original panoramic image of the imaging plane of the tooth row, in the process of eliminating the influence from projection of the cervical vertebrae.

Further, it takes a longer time as a conventional X-ray photographic device is required to construct a plurality of panoramic images in order to construct a single panoramic image.

In addition, as a conventional X-ray photographic device is required to construct panoramic images of a plurality of imaging planes, an imaging plane needs to be repositioned when the distance between the anterior teeth and the cervical vertebrae varies for some patients.

Therefore, the present invention aims to solve aforementioned problems and to provide a technique capable to reduce the influence of the cervical vertebrae projected onto a portion of anterior teeth of a panoramic image of a tooth row.

Solution by the Present Invention

In order to solve above problems, a X-ray photographic device according to the present invention includes: a X-ray generator for irradiating a flux of X-ray to a subject; a X-ray detector to detect a flux of X-ray irradiated from the X-ray generator and transmitted through the subject as an image frame; arms to hold the X-ray generator and the X-ray detector, respectively, facing each other; a rotate-and-slide moving unit that rotates the X-ray generator and the X-ray detector around the subject horizontally, by rotating the arms around a vertical axis, and slides the rotation center of the vertical axis in the horizontal direction at the same time; a photograph control circuit that controls the operation of the rotate-and-slide moving unit; a storage unit that stores image frames detected by the X-ray detector sequentially along the track of a specified imaging plane, by index indicative of the detected order; and an image processing unit for constructing a panoramic image from the image frames through image processing, wherein the image processing unit includes: a pixel-value calculation routine that retrieves each of image frames stored in the storage unit by index and calculates an average value of pixel-values indicative of the brightness of each of pixels, respectively, in the retrieved image frame as an average pixel-value, then stores the average pixel-value for each image frame into the storage unit by index; a reference pixel-value calculation routine that calculates a reference pixel-value for all image frames stored in the storage unit, using at least one of any average pixel-value stored in the storage unit, and stores the result into the storage unit; a pixel-value adjustment-factor calculation routine that calculates a pixel-value adjustment-factor for each of the indices, respectively, based on the inverse of the ratio of each average pixel-value stored in the storage unit by index to the reference pixel-value; and a panoramic image construction routine that constructs a panoramic image by generating each of image frames which brightness is adjusted by multiplying a pixel value of each of pixels by the pixel-value adjustment-factor of the corresponding index respectively in the individual image frames stored in the storage unit by index, and then by superimposing the generated image frames for each of the indices using a shifting amount corresponding to each of the indices.

According to the above configuration, the X-ray photographic device calculates the average pixel-value of an image frame for each of the indices of the image frames in the pixel-value calculation routine. Then, the pixel-value adjustment-factor calculation routine calculates a pixel-value adjustment-factor, based on the inverse of the ratio of the average pixel-value of an image frame to the reference pixel-value. Here, when the reference pixel-value is the minimum value among all of the image frames, for example, the pixel-value adjustment-factor becomes a larger value, as the average pixel-value is smaller. That is, in this case, the pixel-value adjustment-factor becomes a larger value, as the image frame is more pale white overall. Then, the panoramic image construction routine in the X-ray photographic device generates an image frame which brightness is adjusted by multiplying the pixel value of each of pixels by the pixel-value adjustment-factor evenly in the image frame for each of the indices of the image frames. That is, the panoramic image construction routine does not rework original image information in the image frame significantly, rather multiplies all pixels of the image frame by the same value, thereby never missing original image information in the image frame. Also, by this operation, the average brightness of each of image frames can be adjusted at the same level for all image frames. In other words, as the entire image frame is more pale white before the operation, the larger value of the pixel-value adjustment-factor is multiplied, thus enabling to adjust the average brightness of each image frame at the same level for all image frames. The panoramic image construction routine constructs a panoramic image by superimposing these image frames having adjusted brightness. Therefore, the X-ray photographic device can reduce the influence from the cervical vertebrae projected at around the anterior teeth of the panoramic image of a tooth row.

In addition, it is preferable for the pixel-value adjustment-factor calculation routine in the X-ray photographic device according to the present invention includes: an R-value calculation subroutine that divides the reference pixel-value by the average pixel-value of each of the indices, and store an R-value indicative of the result of division in the storage unit; and an averaging process subroutine that calculates the average value of the R-value for a specific index and the R-values for a predetermined number of indices before and after the index, corrects the R-value for the specific index with the calculated average value and stores in the storage unit, and therewith the panoramic image construction routine to multiply the pixel value of each of pixels by the corrected R-value, as the pixel-value adjustment-factor of the corresponding index, in the individual image frames.

According to the above configuration, the X-ray photographic device calculates the R-value for each of the indices of the image frames, in the R-value calculation subroutine, by dividing the reference pixel-value by the average pixel-value. Then, the averaging process subroutine corrects the R-value by the averaging process. Further the panoramic image construction routine generates a panoramic image, using the corrected R-value as the pixel-value adjustment-factor. If the R-value, the inverse of the ratio of the average pixel-value to the reference pixel-value, is used as it is to generate a panoramic image, a pattern in vertical stripes might occur when the R-values are significantly different among indices for consecutive image frames. However, as the X-ray photographic device utilizes the corrected R-value as the pixel-value adjustment-factor for generating a panoramic image, a pattern in vertical stripes in the panoramic image is effectively forestalled.

Furthermore, it is preferable for the pixel-value adjustment-factor calculation routine in the X-ray photographic device according to the present invention includes: an R-value calculation subroutine that divides the reference pixel-value by the average pixel-value of each of the indices and store an R-value indicative of the result of division in the storage unit; and a function estimation subroutine that estimates a hat-shaped function indicative of a hat-shaped curve line smoothly connecting the R-values in the order of the indices, by approximating the R-values for all indices to the predefined hat-shaped curve line, then corrects the R-value to the value by the hat-shaped function and stores in the storage unit, wherein the hat-shaped curve line graphically includes: a predefined length of a first flat portion with a predetermined minimum value; a predefined length of a second flat portion with a predetermined maximum value larger than the first flat portion; a predefined length of a third flat portion with the same value as the first flat portion; a first predefined continuous function connecting the first and second flat portions smoothly; and a second predefined continuous function connecting the second and third flat portions smoothly, and therewith the panoramic image construction routine to multiply the pixel value of each of pixels by the corrected R-value, as the pixel-value adjustment-factor of the corresponding index, in the image frames.

According to the above configuration, the X-ray photographic device calculates the R-value for each of indices of the image frames, in the R-value calculation subroutine, by dividing the reference pixel-value by the average pixel-value. Then, the function estimation subroutine corrects the R-value to each value of the hat-shaped function, by estimating the hat-shaped function for approximating the R-values for all indices. Further the panoramic image construction routine generates a panoramic image, using the corrected R-value as the pixel-value adjustment-factor. As the X-ray photographic device utilizes the corrected R-value as the pixel-value adjustment-factor for generating a panoramic image, a pattern in vertical stripes in the panoramic image is effectively forestalled. In addition, as the X-ray photographic device corrects the R-value by approximating the R-values for all indices to the predefined hat-shaped curve line, it is possible to make correction so that the R-values sorted in the order of indices are smoothly connected, even when a tooth is padded.

Moreover, it is preferable for the pixel-value adjustment-factor calculation routine in the X-ray photographic device according to the present invention includes: an R-value calculation subroutine that divides the reference pixel-value by the average pixel-value of each of the indices and store an R-value indicative of the result of division in the storage unit; an averaging process subroutine that calculates the average value of the R-value for a specific index and the R-values for a predetermined number of indices before and after the index, corrects the R-value for the specific index to the calculated average value and stores in the storage unit; and a function estimation subroutine that estimates a hat-shaped function indicative of a hat-shaped curve line smoothly connecting the corrected R-values in the order of the indices, by approximating the corrected R-values for all indices to the predefined hat-shaped curve line, then corrects the corrected R-value to the value by the hat-shaped function and stores in the storage unit, wherein the hat-shaped curve line graphically includes: a predefined length of a first flat portion with a predetermined minimum value; a predefined length of a second flat portion with a predetermined maximum value larger than the first flat portion; a predefined length of a third flat portion with the same value as the first flat portion; a first predefined continuous function connecting the first and second flat portions smoothly; and a second predefined continuous function connecting the second and third flat portions smoothly, and therewith the panoramic image construction routine to multiply a pixel value of each of pixels by the corrected R-value to the value of the hat-shaped function, as the pixel-value adjustment-factor of the corresponding index, in the individual image frames.

According to the above configuration, the X-ray photographic device calculates the R-value for each of indices of the image frames, corrects the R-value by the averaging process, further corrects to the value of the hat-shaped function, and then generates a panoramic image, by using the further corrected R-value. The X-ray photographic device can effectively forestall a pattern in vertical stripes in the panoramic image.

Additionally, it is preferable for the pixel-value calculation routine in the X-ray photographic device according to the present invention to include; a dark-current component subtraction subroutine that subtracts dark-current components from the detected image frame by the X-ray detector, then stores in the storage unit; and an average pixel-value calculation subroutine that calculates the average pixel-value of the image frame without the dark-current components.

According to the above configuration, the X-ray photographic device subtracts the dark-current components for each of the indices of the image frames, in the dark-current component subtraction subroutine, by subtracting the same value from the entire pixels of each of the image frames, thereby never missing the original image information in each of the image frames. In addition, as the X-ray photographic device calculates the average pixel-value in each of the image frames without the dark-current components, the average pixel-value can be calculated accurately.

Also, it is preferable for the reference pixel-value calculation routine in the X-ray photographic device according to the present invention to calculate the reference pixel-value, by retrieving the average pixel-value of the median of all indices from the storage unit as the minimum value, acquiring the threshold value by multiplying the minimum value by a predetermined coefficient (greater than 1 and less than 2), determining the range of the indices where the average pixel-value is smaller than the threshold value, then averaging a plurality of the average pixel-values in the range of the indices determined hereinabove.

According to the above configuration, the X-ray photographic device can calculate the reference pixel-value from the image frames of the range in the vicinity of the median of all indices, in the reference pixel-value calculation routine. Here, the image frames in the range of the vicinity of the median of all indices correspond to the image frames of the anterior teeth portion that are influenced by the cervical vertebrae much more than image frames of other locations. In this regard, the X-ray photographic device can reduce the influence from the cervical vertebrae effectively, by using image frames in this range to calculate the reference pixel-value.

An image processing method according to the present invention is the method by a X-ray photographic device that includes: a X-ray generator for irradiating a flux of X-ray to a subject; a X-ray detector to detect a flux of X-ray that is irradiated from the X-ray generator and transmitted through the subject, as an image frame; arms to hold the X-ray generator and the X-ray detector, respectively, facing each other; a rotate-and-slide moving unit that rotates the X-ray generator and the X-ray detector around the subject horizontally by rotating the arms around a vertical axis and slides the rotation center of the vertical axis in the horizontal direction at the same time; a photograph control circuit that controls the operation of the rotate-and-slide moving unit; a storage unit that stores image frames detected by the X-ray detector sequentially along the track of a specified imaging plane, by index indicative of the detected order; and an image processing unit for generating a panoramic image from the image frames by image processing, and the method includes and executes: a first step that retrieves image frames stored in the storage unit by index, and calculates an average value of pixel values indicative of the brightness of each of pixels, respectively, in the retrieved image frame, then stores the average pixel-value for each image frame into the storage unit; a second step that calculates a reference pixel-value for all image frames stored in the storage unit, using at least one of any average pixel-value stored in the storage unit, and stores the result into the storage unit; a third step that calculates a pixel-value adjustment-factor for each of the indices, respectively, based on the inverse of the ratio of each average pixel-value stored in the storage unit by index to the reference pixel-value; and a fourth step that generates an image frame which brightness is adjusted by multiplying a pixel value of each of pixels by the pixel-value adjustment-factor of the corresponding index in individual image frames stored in the storage unit by index, and then constructs a panoramic image by superimposing the generated image frames for each of the indices, using a shifting amount corresponding to each of the indices.

According to the above procedure, the image processing method includes steps that the image processing unit calculates the average pixel-value and the pixel-value adjustment-factor of the image frame for each of the indices of image frames, generates each of the image frames which brightness is adjusted by multiplying a pixel value of each of pixels by the pixel-value adjustment-factor in the image frame, and then constructs a panoramic image by superimposing the generated image frames. Therefore, an influence from cervical vertebrae that projects at around the anterior teeth of the panoramic image of a tooth row can be reduced according to the image processing method.

In addition, it is preferable for the image processing method according to the present invention includes in the third step: a division step that divides the reference pixel-value by the average pixel-value of each of the indices, and stores an R-value indicative of the result of division in the storage unit; an averaging step that calculates an average value of the R-value for a specific index and the R-values for a predetermined number of indices before and after the index, corrects the R-value for the specific index with the calculated average value and stores in the storage unit; and a function estimation step that estimates a hat-shaped function indicative of a hat-shaped curve line smoothly connecting the corrected R-values in the order of the indices, by approximating the corrected R-values for all indices to the predefined hat-shaped curve line, then corrects the corrected R-value to the value by the hat-shaped function and stores in the storage unit, wherein the hat-shaped curve line graphically includes: a predefined length of a first flat portion with a predetermined minimum value; a predefined length of a second flat portion with a predetermined maximum value larger than the first flat portion; a predefined length of a third flat portion with the same value as the first flat portion; a first predefined continuous function connecting the first and second flat portions smoothly; and a second predefined continuous function connecting the second and third flat portions smoothly, and therewith the fourth step multiplies a pixel value of each of pixels by the corrected R-value to the value of the hat-shaped function, as the pixel-value adjustment-factor of the corresponding index, in the individual image frames.

According to the above procedure of the image processing method, the image processing unit calculates the R-value for each of index values of the image frames, corrects the R-value by the averaging process, further corrects to the value of the hat-shaped function, and then generates a panoramic image, by using the further corrected R-value. Therefore, a pattern in vertical stripes in the panoramic image can be effectively forestalled according to the above-mentioned image processing method.

In addition, a program according to the present invention is such a program to be executed by a computer for the image processing method. With the configuration hereinabove, the computer installed with this program can realize individual functions provided by the program.

Effects of Invention

According to the present invention, the X-ray photographic device can reduce the influence from the cervical vertebrae projected at around the anterior teeth of the panoramic image of a tooth row, without missing the original image information in the image frames. Also, the X-ray photographic device can reduce the influence from the cervical vertebrae projected at around the anterior teeth of the panoramic image of a tooth row, without influence of different shapes of cervical vertebrae and X-ray permeability by each subject.

In addition, as the X-ray photographic device reduces the influence from the cervical vertebrae projected at around the anterior teeth of the panoramic image of a tooth row by way of arithmetic processing, there is no need to intensify X-ray output in the section corresponding to the anterior teeth, nor decelerate the rotating speed of arms during photographing, and it is possible to suppress the X-ray dose received by the subject.

BRIEF DESCRIPTION OF THE DRAWINGS

FIG. 7A shows the R-values for each of the indices,
and FIG. 7B shows the R-values for each of the indices after correction.
FIG. 8A shows the predefined hat-shaped curve line,
and FIG. 8B shows the corrected R-values for each of the indices, by adapting to the hat-shaped curve line with a solid line, as well as the R-values for each of the indices with a broken line.
FIG. 9 is a flowchart showing an example procedure for constructing a panoramic image by the X-ray photographic device according to an embodiment of the present invention.
FIG. 10A is a panoramic image constructed by a conventional method to superimpose each of image frames,
and FIG. 10B is a panoramic image constructed by adapting the R-values calculated by the processing unit in FIG. 3 to the hat-shaped curve line for correction.

EMBODIMENTS OF THE INVENTION

Hereinafter, an embodiment will be described in detail for carrying out the X-ray photographic device according to the present invention with reference to the accompanying drawings.
[Configuration of the X-Ray Photographic Device]

Figure 1:
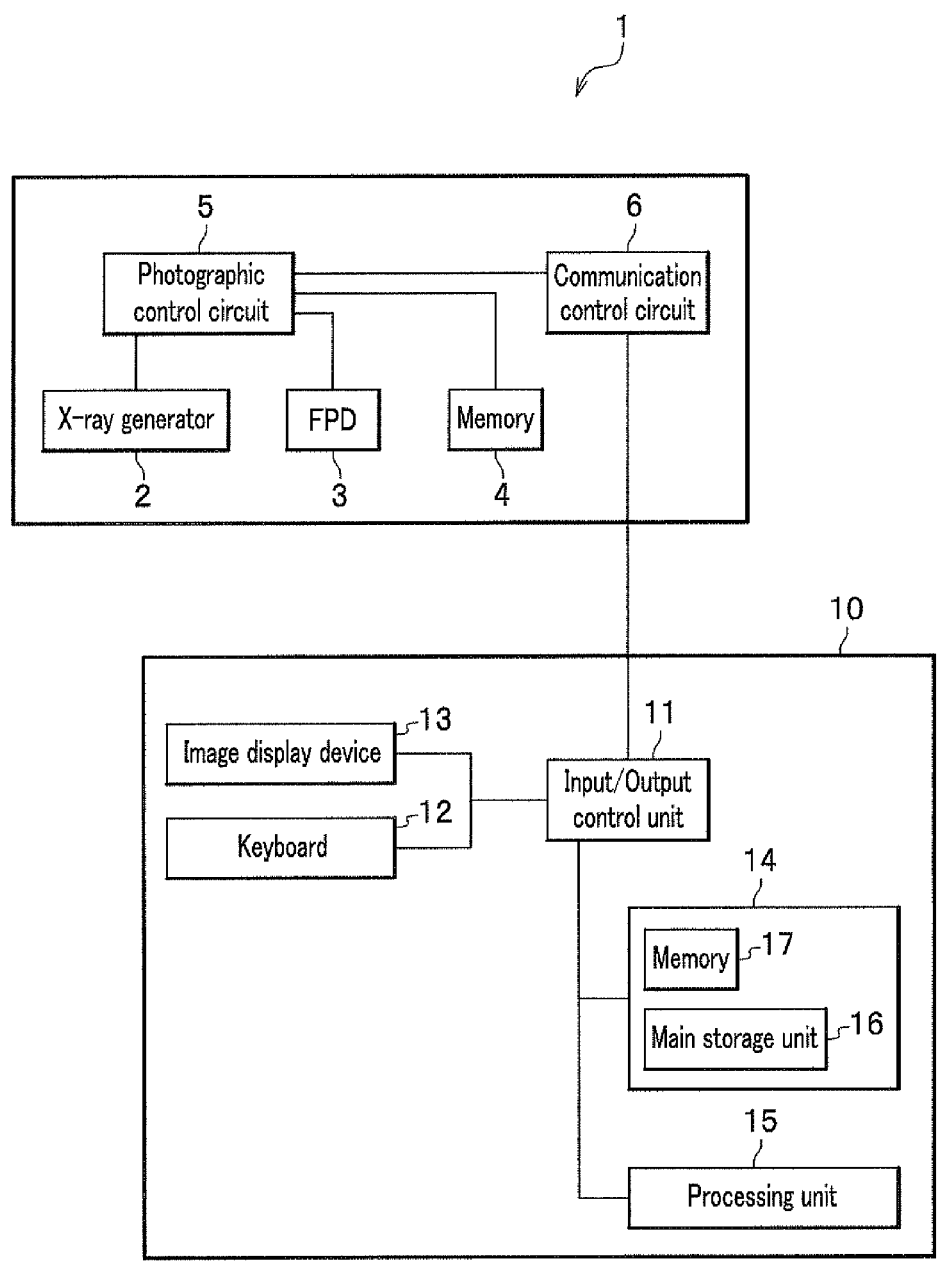
FIG. 1 depicts a block diagram of the configuration of an embodiment according to the present invention.

The X-ray photographic device 1 constructs a panoramic image with a panoramic X-ray tomography method, by taking X-ray image frames of a subject on a given imaging plane. Hereinafter, the subject is described as a tooth row of a person. As shown in FIG. 1, the X-ray photographic device includes a X-ray generator 2, FPD (Flat Panel Detector) 3, a memory 4, a photographic control circuit 5, a communication control circuit 6, and a processing computer 10.

The X-ray generator 2 has a slit (not shown) and irradiates the subject through the slit with slit-shaped X-ray beams at a predetermined timing.

FPD 3 is an X-ray detector which detects X-rays irradiated from the X-ray generator 2 and transmitted through the subject. FPD 3 converts incident X-rays to electric charges, stores in a storage capacitor temporarily, and outputs as electrical signals. FPD 3 photographs the portion of the subject, through which the X-rays are transmitted, at a predetermined frame rate. FPD 3 takes N (4000 to 5000, for example) image frames per shot. The pixel-value of each image frame is represented by luminance values corresponding to the electrical signals, for example.

It is also possible to use other detectors such as a X-ray Image Intensifier (II) or the like, instead of FPD 3. Further candidates for the detection are, for example, a CCD (Charge Coupled Device) image sensor, a CMOS image sensor, a TFT (Thin Film Transistor) sensor, and a CdTe sensor.

The memory 4 is composed of a generic image memory, a hard disk or the like and used to store data temporarily during photographing. The memory 4 stores image frames detected by FPD 3 sequentially along a predetermined trajectory of the imaging plane of the subject, for each index k (k=1 to N) indicative of the detection order. The index k is associated with a particular angle identified by the panoramic photography. After photographing, the data stored in this memory 4 (image frame) is moved to a memory 17 of the processing computer 10 by the communication control circuit 6.

The photographic control circuit 5 is connected with the X-ray generator 2, FPD 3, the memory 4 and the communication control circuit 6, and controls each of them.

Here, an example arrangement of each unit of X-ray photographic device 1 will be described with reference to FIG. 2.

Figure 2:
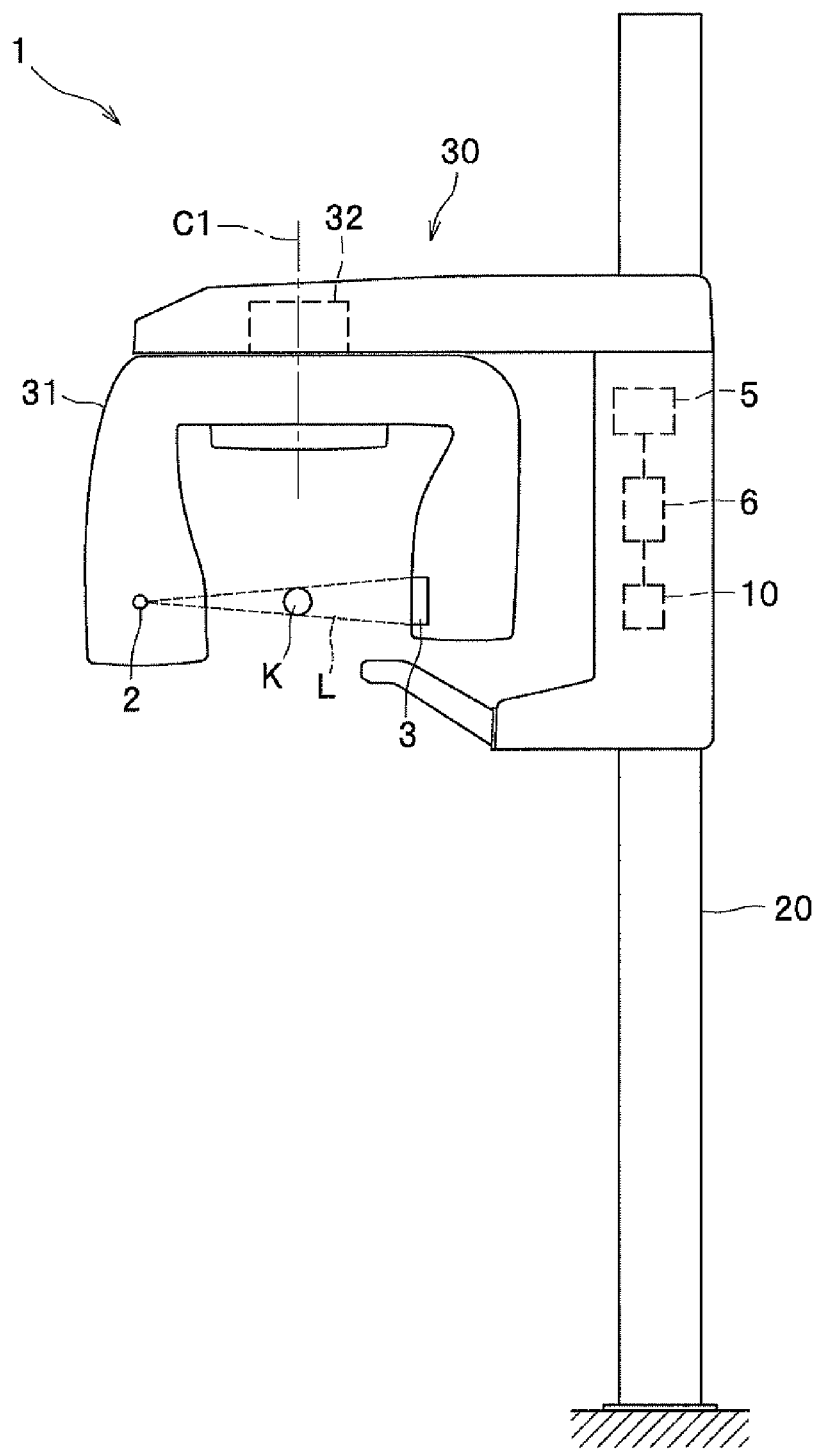
FIG. 2 illustrates a side view of the configuration of an embodiment according to the present invention.

The X-ray photographic device 1 is, as shown in FIG. 2, provided with a support portion 20 and a main body portion 30 that is disposed movably in the support portion 20.

Arranged in the support portion 20, for example, are photographic control circuit 5, the communication control circuit 6 and a control unit that includes the processing computer 10.

The main body portion 30 includes an arm 31 and a rotate-and-slide moving unit 32.

The Arm 31 is rotatably disposed around the arm rotation center axis C1, which is a vertical axis. The Arm 31 holds an X-ray irradiation unit of the X-ray generator 2 and a light-receiving surface of the FPD 3, facing each other at a predetermined distance. Thus, FPD 3 detects a flux of X-ray L, irradiated from the X-ray generator 2 and transmitted through the subject K, as an image frame F.

The rotate-and-slide moving unit 32 rotates the arm 31 around a vertical axis at a predetermined angular speed by driving motors and actuators. Thus, the rotate-and-slide moving unit 32 rotates the X-ray generator 2 and the FPD 3, both held to the arm 31, horizontally around the subject K. In addition, the rotate-and-slide moving unit 32 is configured to allow sliding movement of the vertical rotation-center axis in the horizontal direction. Note that it is the photographic control circuit 5 that controls the operation of the rotate-and-slide moving unit.

Returning to FIG. 1, the description of the structure of the X-ray photographic device will continue.

The processing computer 10, as shown in FIG. 1, includes an input/output control unit 11, a keyboard 12, an image display device 13, a storage unit 14, and a processing unit (image processing unit) 15.

The input/output control unit 11 is intended to control for inputting commands from the keyboard 12 or the like to the processing unit 15, or for outputting the process result of the processing unit 15 to the image display device 13. Further, the input/output control unit 11 controls for inputting data from the communication control circuit 6 to the storage unit 14, or outputting data already processed and stored in the storage unit 14 to the communication control circuit 6.

The keyboard 12 is an input device to enter commands or the like to the processing unit 15. Note that an input device may be constituted by a mouse or a touch panel.

The image display device 13 is an output device that outputs the processing result of the processing unit 15 and composed of a liquid crystal display or the like.

The storage unit 14 is composed of a RAM (Random Access Memory), a ROM (Read Only Memory), a HDD (Hard Disk Drive) or the like, providing a main storage device 16 and a memory 17.

The main memory unit 16, for example, stores an image processing program or the like for the processing unit 15 to operate. In addition, the main storage device 16 has a memory area or the like used to construct a panoramic image.

The memory 17 is composed of a generic image memory, a hard disk or the like, and intended to retrieve data temporarily stored in the memory 4 during photographing and then store the retrieved data. That is, the memory 17 stores image frames detected by the X-ray detector 3 sequentially along a predetermined trajectory of the imaging plane of the subject K, for each of indices "k" (k=1 to N) indicative of the detection order. In addition, the memory 17 stores the process result of the processing unit 15 temporarily.

The processing unit 15 (image processing unit) is to generate a panoramic image from the image frames through image processing. The processing unit 15 is, for example, composed of a CPU (Central Processing Unit) and a FPGA (Field Programmable Gate Array), and executes a specified program loaded in the RAM for a function to be described later. This program may be provided via a communication line, or recorded and distributed in a recording medium such as CD-ROM.

Figure 3:
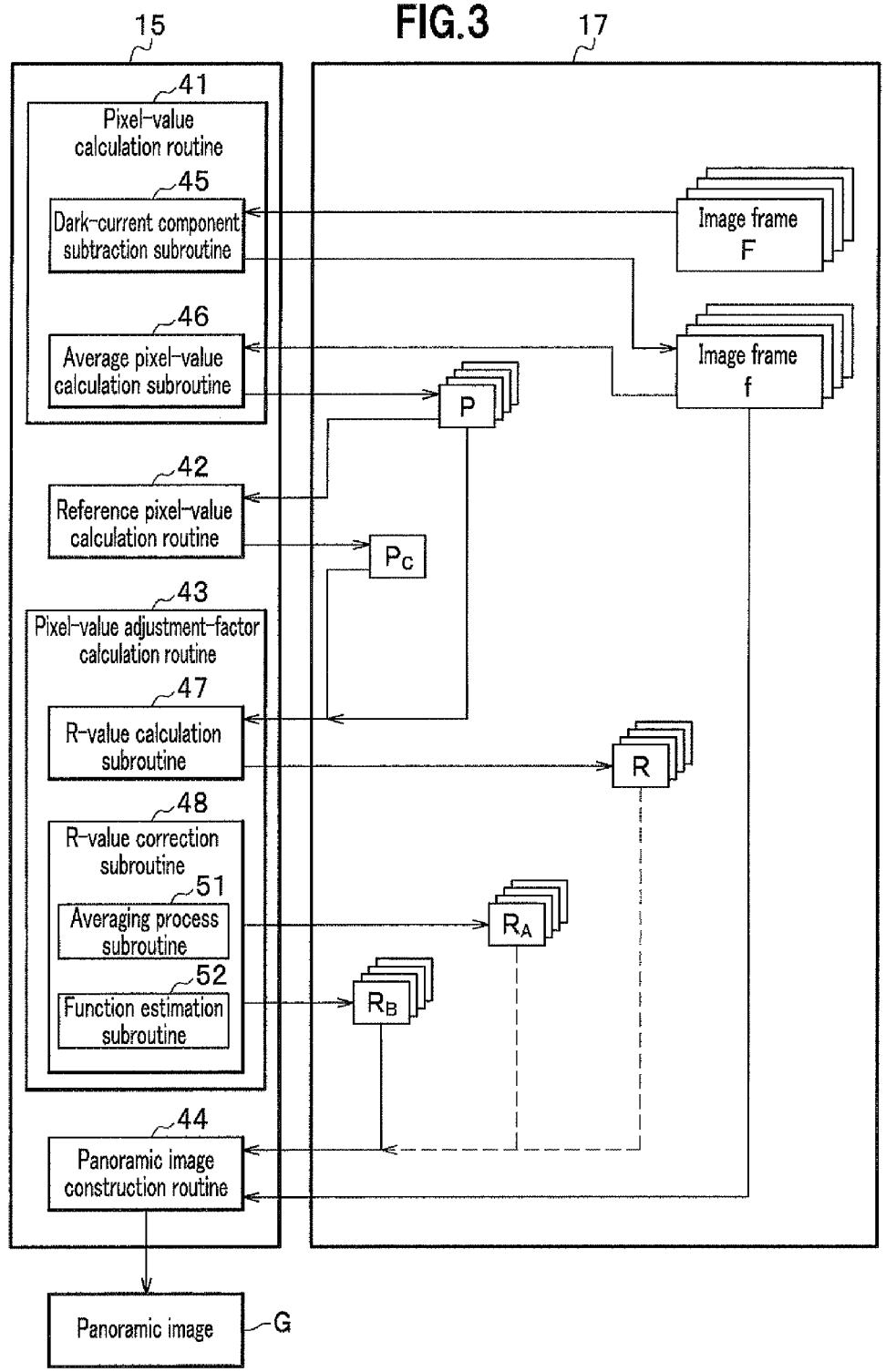
FIG. 3 depicts a block diagram of the functions of the processing unit of the process computer shown in FIG. 1.

The processing unit 15 includes, as shown in FIG. 3, a pixel-value calculation routine 41, a reference pixel-value calculation routine 42, a pixel-value adjustment-factor calculation routine 43, and a panoramic image construction routine 44.

The pixel-value calculation routine 41 is to retrieve the image frame stored in the memory 17 for each index "k" and to calculate the average value of the pixel-values indicative of the brightness of each of pixels in the retrieved image frame, as the average pixel-value. The calculated average pixel-value of each of the image frames is stored in the memory 17 for each index "k".

In this embodiment, the pixel-value calculation routine 41 includes a dark-current component subtraction subroutine 45 and an average pixel-value calculation subroutine 46.

The dark-current component subtraction subroutine 45 subtracts dark-current components from the detected image frame by the FPD 3, then stores in the memory 17.

The average pixel-value calculation subroutine 46 calculates the average pixel-value P of the image frame without the dark-current components.

Hereinafter, a simple X-ray image detected by the FPD 3 is referred to as an image frame F, and an offset X-ray image obtained by subtracting the dark-current components therefrom, as an image frame "f".

The reference pixel-value calculation routine 42 is to calculate a reference pixel-value Pc for all image frames "f" stored in the memory 17, using any one of the average pixel-value P stored in the memory 17. The calculated reference pixel-value Pc is stored in the memory 17.

In the present embodiment, the reference pixel-value calculation routine 42, for example, retrieves the average pixel-value P of the median of all indices "k" (1 to N) from the memory 17 to be assumed as the minimum value, then searches all image frames within the range having the average pixel-value P up to the predetermined threshold value, for later usage. Further, the reference pixel-value calculation routine 42 acquires the threshold value by multiplying the retrieved minimum value by a predetermined coefficient "c", determines the range of the index "k" in which the value of the average pixel-value P is smaller than the threshold value, then calculates the reference pixel-value Pc by averaging a plurality of the average pixel-values P within the determined range of the index "k". Here, the predetermined coefficient "c" can be any value that is greater than 1 and smaller than 2, so the value c=1.25 can be used, for example.

The pixel-value adjustment-factor calculation routine 43 is to calculate a pixel-value adjustment-factor for each of the indices "k", based on the inverse of the ratio of the average pixel-value P to the reference pixel-value Pc for each of the indices "k" stored in the memory 17. The pixel-value adjustment-factor is a factor for adjusting pixel-values of an image frame "f", by multiplying the pixel-values of the image frame by the factor.

In the present embodiment, the pixel-value adjustment-factor calculation routine 43 includes an R-value calculation subroutine 47 and an R-value correction subroutine 48.

The R-value calculation subroutine 47 is to divide the reference pixel-value Pc by the average pixel-value P of each index "k". The R-value indicative of the result of division is the coefficient corresponding to each image frame, and dimensionless number representative of the concentration ratio. The calculated R-values are stored in the memory 17. This R-value itself may be used as the pixel-value adjustment-factor.

The R-value correction subroutine 48 includes an averaging process subroutine 51 and a function estimation subroutine 52.

The averaging process subroutine 51 calculates the average value of the R-value for a specific index "k" and the R-values for a predetermined number "n" of indices before and after the index "k", corrects the R-value for the specific index "k" to the calculated average value. The averaging process subroutine 51 repeats the same operation for each of the indices. Here, "n" is any integer greater than or equal to 1. The R-value corrected hereinabove is referred to as $R_A$. $R_A$ is stored in the memory 17. This $R_A$ can be also used as the pixel-value adjustment-factor.

The function estimation subroutine 52 retrieves the R-value or the corrected R-value ($R_A$) from the memory 17, and estimates a hat-shaped function indicative of a hat-shaped curve line smoothly connecting the retrieved R-values in the order of the index "k", then corrects the R-value to the value by the hat-shaped function for each index "k". The R-value corrected hereinabove is referred to as $R_B$. $R_B$ is stored in the memory 17. This $R_B$ can be also used as the pixel-value adjustment-factor.

In the present embodiment, the function estimation subroutine 52 is designed in such a way that it estimates the hat-shaped function by approximating the R-values for all indices "k" to the predefined hat-shaped curve line, then uses $R_B$ as the pixel-value adjustment-factor. Note that the detail processing will be described later for the function estimation subroutine 52.

The panoramic image construction routine 44 is to construct a panoramic image by superimposing the image frames using a shifting amount corresponding to each of the index "k", respectively, after adjusting the pixel values of the image frame stored in the memory 17 for each of indices "k". The panoramic image construction routine 44 generates each of image frames which brightness is adjusted by multiplying the pixel-value of each of pixels by the pixel-value adjustment-factor ($R_B$) of the corresponding index "k" evenly in individual image frames. Note that the shifting amount for each of the image frames is obtained by a known method for generating a panoramic image according to the trajectory of the imaging plane. A panoramic image G constructed hereinabove is stored in the main storage device 16 and also displayed on the image display device 13.

[Specific Example of the Average Pixel-Value Calculation Method]

Figure 4:
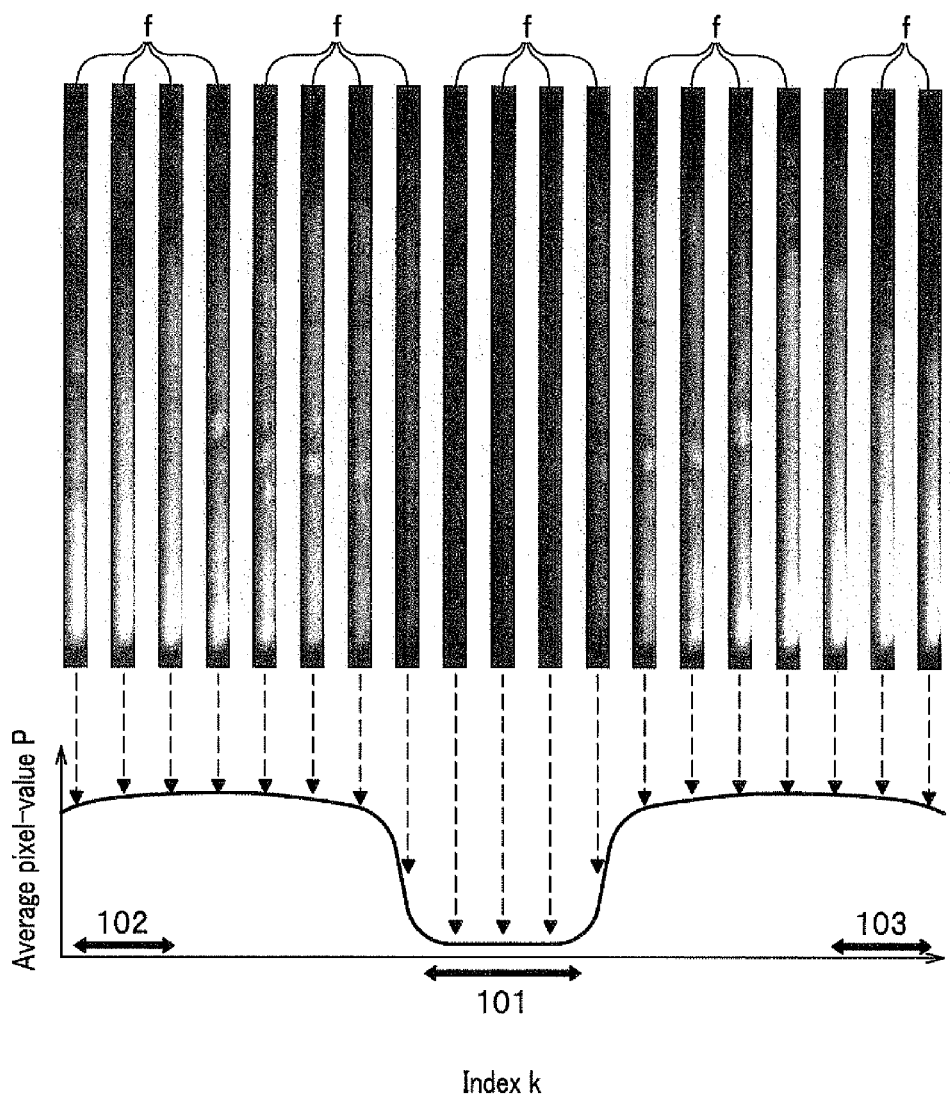
FIG. 4 is a graph showing an example of average pixel-values calculated by the processing unit in FIG. 3 for each of the indices of the image frames.

Specific example of a calculation method of the average pixel-value will be described with reference to FIG. 4. FIG. 4 is a graph showing an example of the average pixel-value calculated by the processing unit in FIG. 3 for each of the indices corresponding to the image frames respectively. The anterior teeth portion is to be projected in the horizontal center of the panoramic image finally constructed. As an example of an image frame before constructing the final panoramic image, FIG. 4 shows a plurality of vertically-elongated strip-shaped image frame "f", with dark-current components eliminated. Note that the number of image frame "f" is about 4000 to 5000 in practice.

In FIG. 4, an index "k" is associated with a particular angle identified by the panoramic photographing. For example, a region indicated by a reference numeral 101 in the vicinity of the median of all indices "k" corresponds to the anterior teeth portion. In addition, a region indicated by a reference numeral 102 in the vicinity of the minimum value of all indices "k" corresponds to one temporomandibular joint, and a region indicated by a reference numeral 103 in the vicinity of the maximum value of all indices "k" corresponds to the other temporomandibular joint.

The average pixel-value calculation subroutine 46 calculates the value P obtained by averaging the pixel-values for all pixels in the image frame for each image frame "f". This P is referred to as an average pixel-value of an image frame. For example, if one strip-shaped image frame "f" is composed of 1000 pixels of 10 horizontal pixels×100 vertical pixels, the average pixel-value calculation subroutine 46 averages pixel-values of 1000 pixels as a whole.

As a modification of the average pixel-value calculation subroutine 46, pixels in one image frame "f" may be thinned out for averaging. In this case, for example, the average pixel-value calculation subroutine 46 may average 250 pixels of 5 pixels×50 pixels by skipping every other pixel, for the aforementioned 1000-pixel image.

A pixel value is a luminance value, for example. If it is 12-bit scale, for example, it can be represented with a number of 0 to 4095.

As shown at the lower part of FIG. 4, a curve line connecting the average pixel-values P in the order of the index "k" of the image frames shows the values in the regions indicated by the reference numerals 102 and 103 are high, and the values in the region indicated by the reference numeral 101 are low. In the region indicated by the reference numeral 101, the image frames are whitish as a whole.

[Specific Example of the Reference Pixel-Value Calculation Method]

Figure 5:
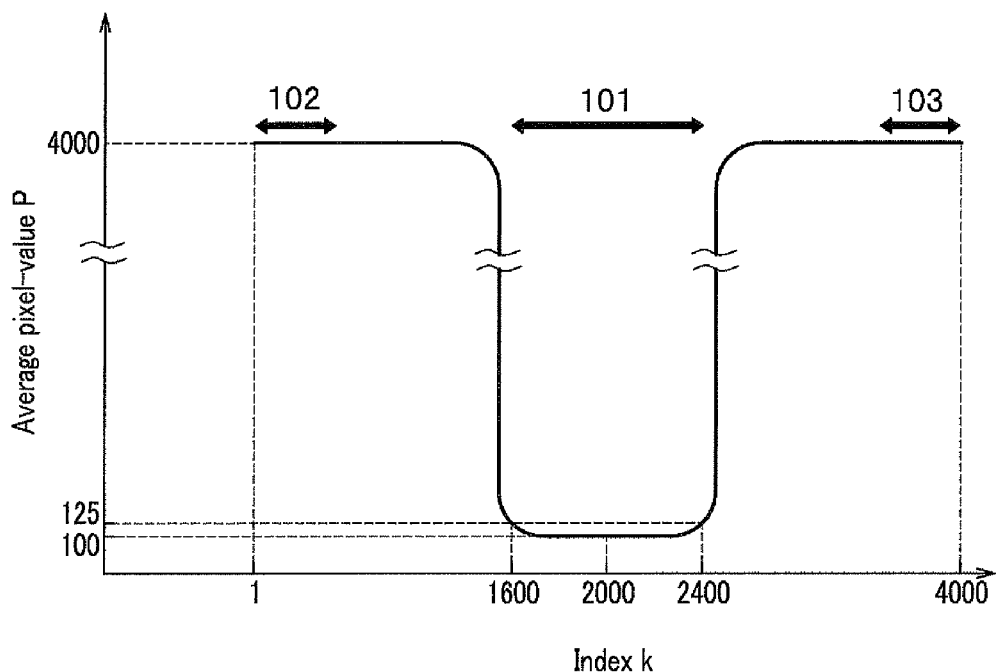
FIG. 5 is a graph showing another example of average pixel-values calculated by the processing unit in FIG. 3 for each of the indices of the image frames.

Next, a specific example of the method will be described, by referring to FIG. 5, for the reference pixel-value calculation routine 42 to calculate a reference pixel-value by determining the range of the image frames having projection of the cervical vertebrae, in the region indicated by the reference numeral 101 where the cervical vertebrae may be projected. FIG. 5 is a graph showing another example of the average pixel-value calculated by the processing unit in FIG. 3, for each of the indices of the image frames. Let's assume 4000 image frames, for example. In order to find the position of the image frames corresponding to the anterior teeth portion, the reference pixel-value calculation routine 42 first refers to the average pixel-value P of the image frame positioned at the half of whole indices, the $2000^{th}$ image frame, for example, as a reference value. Let's also assume that the average pixel-value P of the $2000^{th}$ image frame is "100". In this case, assuming that the predetermined coefficient is 1.25, for example, the threshold value is calculated as "125" by the reference pixel-value calculation routine 42.

Then, the reference pixel-value calculation routine 42 searches for the average pixel-values P in the descending order of the indices from the 2000$^{th}$ image frame, to determine the range of the indices having the average pixel-value equal to or less than the threshold value. Thus, the index of one boundary is determined to be the 1600$^{th}$, for example, where the average pixel-value P is equal to or less than "125".

Also, the reference pixel-value calculation routine 42 searches for the average pixel-values P in the ascending order of the indices from the 2000$^{th}$ image frame, to determine the range of the index values having the average pixel-value equal to or less than the threshold. Thus, the index of the other boundary is determined to be the 2400$^{th}$, for example, where the average pixel-value P is equal to or less than "125".

Accordingly, the reference pixel-value calculation routine 42 determines that 801 image frames of 1600$^{th}$ to 2400$^{th}$ are the image frames in the range of the anterior teeth.

Then, the reference pixel-value calculation routine 42 obtains an average value as the reference pixel-value $P_C$, by averaging the values of the respective average pixel-values P of the 801 image frames.

In this way, the reference pixel-value calculation routine 42 determines the position of the image frame where the projection of the cervical vertebrae begins to occur, and the position of the image frame where such projection no longer occurs, by searching the range of the image frames determined to be whitish out of the whole image frames, toward the left of the image frame detected at the center position in the FIG. 4 then in the same way for the right direction.

Figure 6:
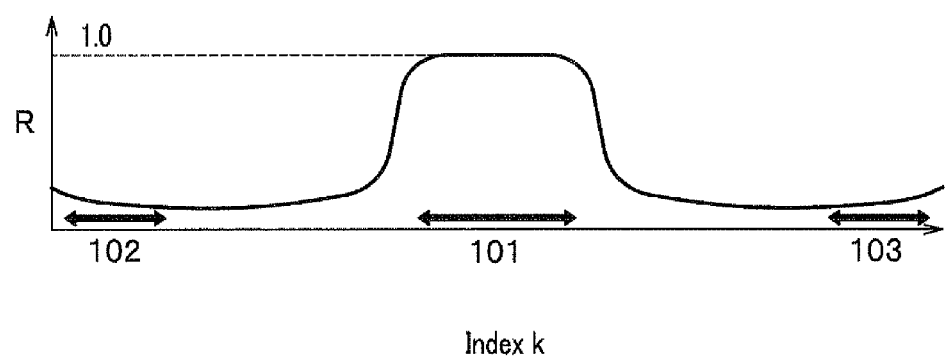
FIG. 6 is a graph showing an example of the R-values calculated by the processing unit in FIG. 3 for each of the indices of the image frames.

FIG. 6 shows an example of the R-value which the R-value calculation subroutine 47 obtained by dividing the reference pixel-value $P_C$ calculated by the reference pixel-value calculation routine 42, by the average pixel-value P of each index "k". It should be noted that this R-value corresponds to the average pixel-value P shown at the lower side of FIG. 4.

[First R-Value Correction Method]

Figure 7A:
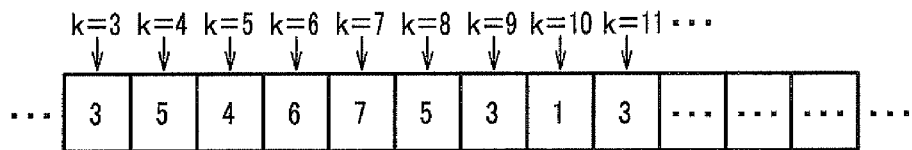
FIGS. 7A and 7B depict an example of the processing method for correcting the R-values calculated by the processing unit in FIG. 3, where
Figure 7B:
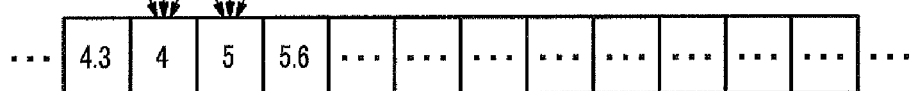

As a first R-value correction method, a specific example of the averaging process subroutine 51 will be described with reference to FIG. 7. FIGS. 7A and 7B depict an example of the processing method for correcting the R-values calculated by the processing unit in FIG. 3, where FIG. 7A shows the R-values for each of the indices and FIG. 7B shows the R-values for each of the indices after correction. As shown in FIG. 7A, when the R-value is "5" for the index "k" of 3 and the R-values before and after that are "3" and "4", for example, the average R-value becomes "4" for the index "k" of 3 to 5. By this averaging process, when the index "k" is 4, for example, the R-value is updated from "5" to "4". In addition, the averaging result of the R-values for the index "k" of 4 to 6 becomes "5". By this averaging process, when the index "k" is 5, for example, the R-value is updated from "4" to "5". The averaging process is performed in a similar manner for others.

Using the above method, a smooth curve line can be obtained when connecting the R-values in the order of the index "k". Consequently, it is possible to enhance the quality of a panoramic image, when generating it by adjusting the pixel-values of the image frames. In case the R-values are significantly different in successive indices of the image frames, a pattern of vertical stripes may occur if a panoramic image is generated using those R-values as they are. However, the X-ray photographic device 1 can effectively forestall a pattern of vertical stripes in the panoramic image, by being able to generate a panoramic image using the R-value corrected by the averaging process subroutine 51 as the pixel-value adjustment-factor.

Further, averaging was made in this example on the three R-values, for the specified index and before and after that, but more R-values may be used. If averaging is made on dozens of R-values, by adding 20 to 30 respectively before and after the specified index, for example, the influence can be eliminated even when a tooth is padded.

[Second R-Value Correction Method]

Figure 8A:
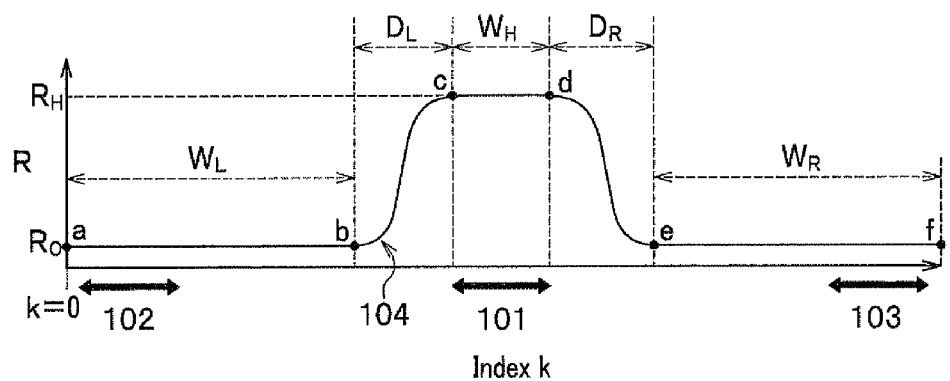
FIGS. 8A and 8B depict another example of the processing method for correcting the R-values calculated by the processing unit in FIG. 3, where
Figure 8B:
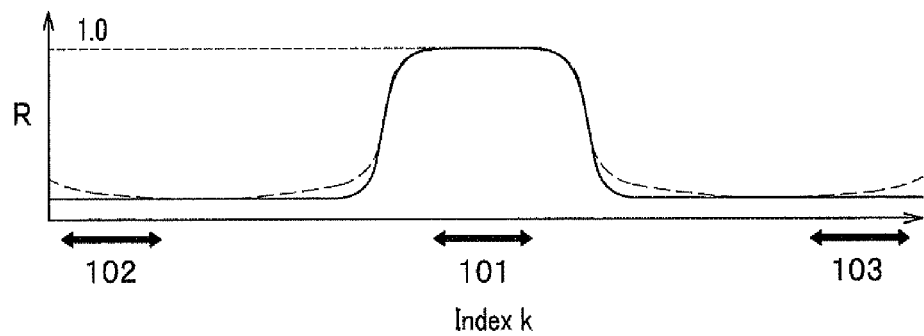

As a second method of correcting the R-value, a specific example of the operation of the function estimation subroutine 52 will be described with reference to FIGS. 8A and 8B. FIGS. 8A and 8B are diagrams showing another example of a processing method for correcting the R-value calculated by the processing unit in FIG. 3, where FIG. 8A shows the predefined hat-shaped curve line and FIG. 8B shows the corrected R-values for each of the indices, by adjusting to the hat-shaped curve line in a solid line, as well as the R-values for each of the indices in a broken line.

Here, the hat-shaped curve line is, for example, a curve line that passes through each of points "a", "b", "c", "d", "e", and "f", as shown in FIG. 8A. Here, a region between the points "a" and "b" is referred to as a first flat portion, a region between the points "c" and "d" as a second flat portion, and a region between the points "e" and "f" as a third flat portion. At this time in the curve line, the parameters defined in (A1) through (A5) below are provided, respectively. Note that the value of the vertical direction of the curve line corresponds to the R-value.

(A1) A length $W_L$ of the first flat portion indicating a predetermined minimum value $R_0$ (A2) A length $W_H$ of the second flat portion indicating a predetermined maximum value $R_H$ greater than the first flat portion (A3) A length $W_R$ of the third flat portion indicating the same value as the first flat portion (A4) An inclination $D_L$ of the first continuous function indicating a curve line smoothly connecting the first and second flat portions (A5) A declination $D_R$ of the second continuous function indicating a curve line smoothly connecting the second and third flat portions Here, as the initial setting of the first and second continuous functions, for example, one cycle of a curve line of the cosine function from phase $-\pi/2$ to $+\pi/2$ can be divided into two half cycles for defining the first and second continuous functions. Note that the first continuous function is defined by the inclination from the point "b" to the point "c" as indicated by a reference numeral 104. Likewise, the second continuous function is defined by the inclination from the point "e" to the point "d".

The function estimation subroutine 52 accumulates the absolute values of the difference between each calculated R-value of all the indices "k" and each of the R-values on the predefined hat-shaped curve line, then determines the hat-shaped curve line by the least squares method, for example, so that the cumulative value becomes minimum. The function estimation subroutine 52 obtains R-values ($R_B$) corresponding to each of the indices on the determined hat-shaped curve line.

Here, the factors that determine the hat-shaped curve line to be set in accordance with each subject (the person) are the parameters of the R-value of the first flat portion (the minimum value $R_0$), the inclination of the first continuous function and the length $W_H$ of the second flat portion.

[Flow of Panoramic Image Construction]

A procedure for constructing a panoramic image by X-ray photographic device 1 will be described with reference to FIG. 9.

First, a patient (subject) is positioned (step S1). Here, a method of positioning the patient (subject) to the X-ray photographic device 1 is, for example, performed by fixing the patient to a chin rest.

Then, X-ray photographing is performed (step S2). Here, once a photographing start switch (not shown) is pressed, a series of the operations is repeated N times, while shifting the irradiation position of the X-ray, such that the arm 31 is moved to a position of the X-ray irradiation, the X-rays are irradiated from the X-ray generator 2, and the X-rays transmitted through a subject is detected by the FPD, thereby completing one X-ray photographing for the patient (subject) (index k=1 to N). During photographing, the image frame for each of the indices "k" (plain X-ray image) is temporarily stored in the memory 4. After completion of photographing, the communication control circuit 6 transfers image frames stored in the memory 4 to the processing computer 10. The processing computer 10 stores the image frame F for each of the indices "k" in the memory 17 (step S3).

Then, the dark-current component subtraction subroutine 45 in the processing unit 15 of the processing computer 10 retrieves the image frame F (plain X-ray image) for each of the indices "k" from the memory 17, eliminates dark-current components from the retrieved image frame, and then stores this image frame "f" (offset X-ray image) in the memory 17 (step S4).

Next, the average pixel-value calculation subroutine 46 in the processing unit 15 retrieves the image frame "f" (offset X-ray image) for each of the indices "k" from the memory 17, calculate the average pixel-value P of the retrieved image frame, and stores this average pixel-value P in the memory 17 (step S5).

Next, the reference pixel-value calculating routine 42 in the processing unit 15 retrieves the average pixel-value P of the index "k" at the position of N/2 from the memory 17, and determines the anterior teeth portion 101 (see FIG. 5). Then, the reference pixel-value calculating routine 42 calculates the reference pixel-value $P_C$ for all image frames "f" (average pixel-value for the anterior teeth portion), by averaging a plurality of the average pixel-values P identified by the indices "k" for the anterior teeth portion 101, and then stores in the memory 17 (step S6).

Next, the R-value calculation subroutine 47 in the processing unit 15 retrieves the reference pixel-value $P_C$ (average pixel-value for the anterior teeth portion) and then the average pixel-value P for each of the indices "k" from the memory 17, calculates $R=P_C/P$ for each of the indices "k", and stores in the memory 17 (step S7).

Then, the averaging process subroutine 51 of the R-value correction subroutine 48 in the processing unit 15 retrieves the R-value for each of the indices "k" from the memory 17, corrects the R-value to $R_A$ by averaging the R-value curve line for the index "k", then stores in the memory 17 (step S8).

Then, the function estimation subroutine 52 of the R-value correction subroutine 48 retrieves $R_A$ for each of the indices "k" from the memory 17 and estimates a function representative of $R_A$ curve line for the index "k", then corrects it to $R_B$ and stores in the memory 17 (step S9).

Then, the panoramic image construction routine 44 in the processing unit 15 retrieves the corrected R-value ($R_B$) for each of the indices "k" and the image frame for the corresponding index "k" from the memory 17, generates an image frame having adjusted pixel-values, by multiplying each of the pixel-values of the pixels in the retrieved image frame by the corrected R-value ($R_B$), then constructs a panoramic image G by superimposing the image frames generated for each of the indices "k" and stores in the memory 17 (step S10).

Then, the panoramic image construction routine 44 retrieves the panoramic image G from the memory 17, and outputs it on the image display device 13 (step S11).

A panoramic image is constructed in the above procedure.

Note that it was assumed and described such that the processing unit 15 executes all the steps S7 through S10 in this order, but a part of them could be eliminated as (B1) through (B3) below.

(B1) Eliminate Step S9
(B2) Eliminate Step S8
(B3) Eliminate Steps S8 and S9

[Specific Examples of Panoramic Image]

Figure 10A:
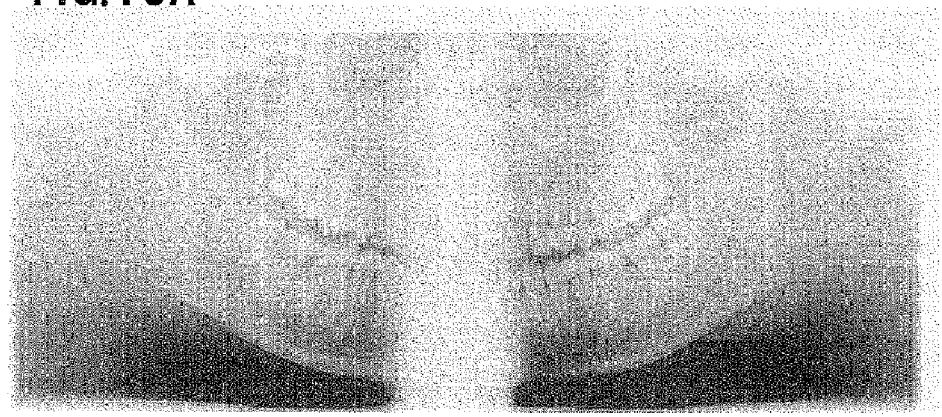
FIGS. 10A and 10B depict an example of a panoramic image, where
Figure 10B:
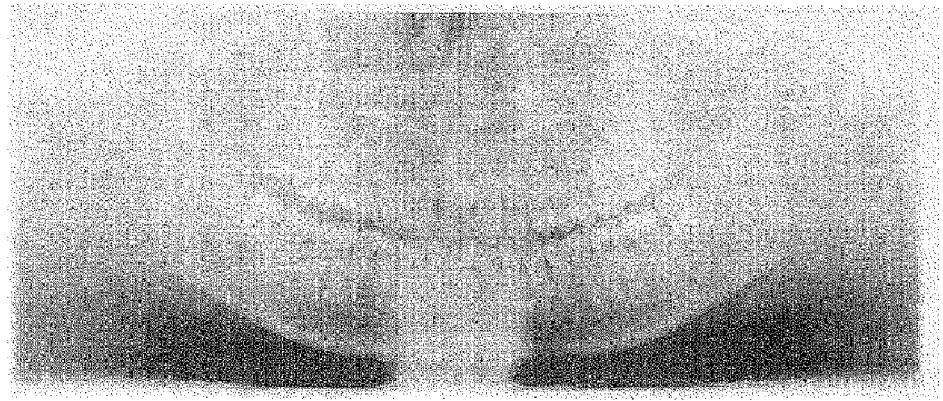
Figure 11:
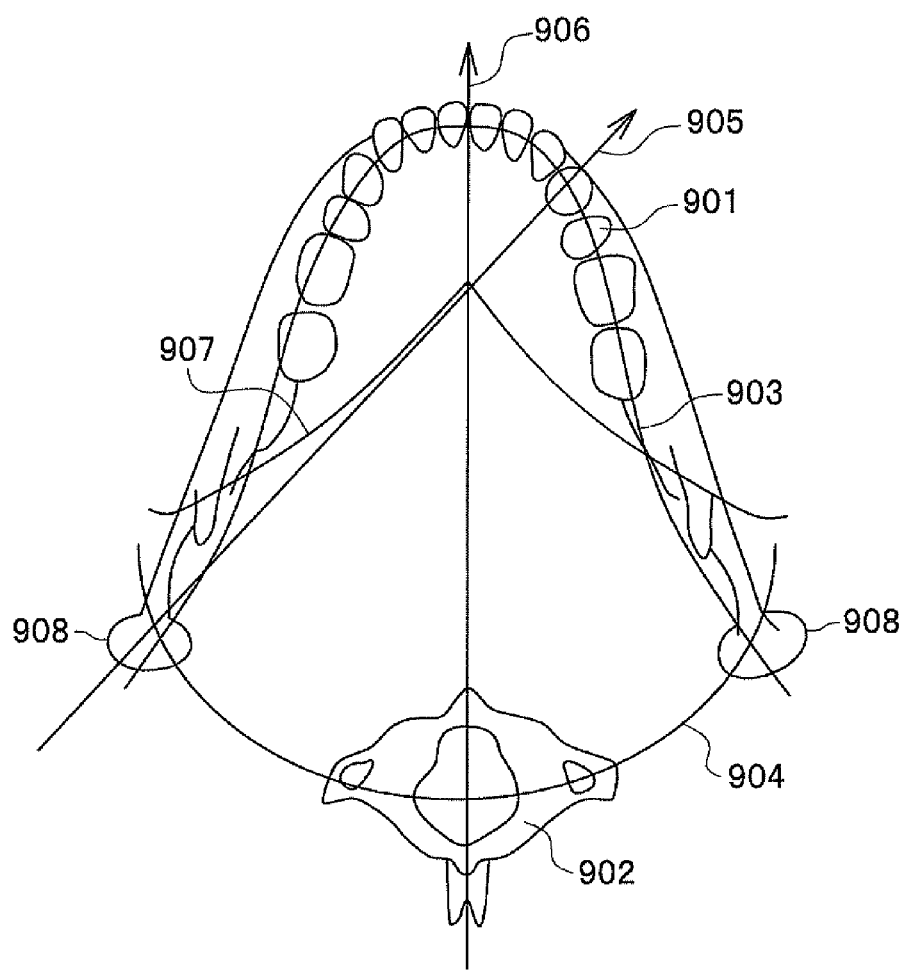
FIG. 11 illustrates a chart explaining the principle for a conventional X-ray photographic device to construct a panoramic image of tooth row by eliminating the influence from the cervical vertebrae.

FIGS. 10A and 10B depict examples of a panoramic image, where FIG. 10A is a panoramic image constructed by a conventional method to superimpose each of image frames, and FIG. 10B is a panoramic image constructed by adapting the R-values calculated by the processing unit in FIG. 3 to the hat-shaped curve line for correction.

In general, it means that a subject for making the X-ray difficult to transmit through is placed in the path of X-ray beams, within the angles of photographing the anterior teeth portion via the cervical vertebrae by the X-ray photographic device. Since X-rays having high-frequency energies survive in this area, a beam hardening phenomenon occurs that makes the difference of the X-ray intensity smaller in the real anterior teeth portion. Therefore, the difference of the shades obtained at the light-receiving surface of the FPD becomes also small in the image frames for the anterior teeth portion. For this reason, as shown in FIG. 10A, a solid white image is generated at the anterior teeth portion of the panoramic image in the conventional method.

On the other hand, the X-ray photographic device 1 according to the present embodiment performs a multiplication operation, emphasizing the contrast of the image frames of the indices in the section corresponding to the anterior teeth portion. Therefore, as shown in FIG. 10B, an image having clear shade is obtained in the anterior teeth portion of the panoramic image. In other words, the X-ray photographic device 1 could reduce the influence of the cervical vertebrae projected in anterior teeth portion of the panoramic image of the tooth rows. At this time, as the multiplication operation for the image by the X-ray photographic device 1 is performed by multiplying all pixels in an image frame by the same pixel-value adjustment-factor, the image information provided in the original image frame is prevented from missing.

According to the present embodiment, the X-ray photographic device 1 can eliminate the influence of the cervical vertebrae projected in the anterior teeth portion of the panoramic image of a tooth row, without constructing panoramic images of a plurality of the imaging planes.

Also, the X-ray photographic device 1 can eliminate the influence of the cervical vertebrae projected in the anterior teeth portion of the panoramic image of a tooth row, independent from the individual differences in patients such as the shape of cervical vertebrae and X-ray permeability.

In addition, according to the present embodiment, the X-ray photographic device 1 constructs a panoramic image while performing a process to eliminate the influence of the cervical vertebrae, based on the image frames moved and stored in the memory 17 of the processing computer 10 after the X-ray photographing, then stores again in the memory 17 of the processing computer 10. Therefore, a special workspace is not required to eliminate the influence of the cervical vertebrae from the panoramic image.

Hereinabove, an embodiment according to the present invention was described, but the present invention is not limited to this and can be implemented in a scope that does not change the spirit. For example, in the present embodiment, $R_B$ was used as the pixel-value adjustment-factor by approximating the R-values for all indices "k" to the predefined hat-shaped curve line then estimating the hat-shaped function, but the R-value calculated in the R-value calculation subroutine 47 may be used as the pixel-value adjustment-factor without correction.

In addition, when correcting the R-value, $R_A$ of the corrected R-value by the averaging process subroutine 51 may be used as the pixel-value adjustment-factor.

Further, a double correction $R_B$ may be used as the pixel-value adjustment-factor, by approximating the $R_A$ for all indices "k" to the predefined hat-shaped curve line then estimating the hat-shaped function.

In addition, it was decided in the present embodiment to include the dark-current component subtraction subroutine 45 in the processing unit 15, but the average pixel-value calculation subroutine 46 may calculate the average pixel-value P in the image frame F, if there is no dark-current components contained in the image frame F detected by the FPD 3, or at negligible level.

Furthermore, the reference pixel-value calculation routine 42 was designed to search for the range of the indices "k" to calculate the reference pixel-value $P_C$, by using the average pixel-value P of the median of all indices "k" (1 to N), but it is arbitrary to use the average pixel-value P corresponding to any position among all image frames, or the average pixel-value P of any index "k". The employed number of the average pixel-values P may be at least one or more. Further, the employed number of the average pixel-values P may be determined in advance or during the process.

Moreover, it has been described that the processing computer 10 is incorporated in the control unit provided in the support portion 20 of the X-ray photographic device 1, but it may be a personal computer or the like disposed outside the control unit and connected via a cable.

LEGEND FOR REFERENCE NUMERALS

1 X-ray photographic device
2 X-ray generator
3 FPD (X-ray detector)
4 Memory
5 Photographic control circuit
6 Communication control circuit
10 Processing computer
11 Input/Output control unit
12 Keyboard
13 Image display device
14 Storage unit
15 Processing unit
16 Main storage device
17 Memory
20 Support portion
30 Main body portion
31 Arm
32 Rotate-and-slide moving unit
41 Pixel-value calculation routine
42 Reference pixel-value calculation routine
43 Pixel-value adjustment-factor calculation routine
44 Panoramic image construction routine
45 Dark-current component subtraction subroutine
46 Average pixel-value calculation subroutine
47 R-value calculation subroutine
48 R-value correction subroutine
51 Averaging process subroutine
52 Function estimation subroutine

What is claimed is:

1. a X-ray photographic device comprising:
a X-ray generator for irradiating a flux of X-ray to a subject;
a X-ray detector to detect the flux of X-ray, that is irradiated from the X-ray generator and transmitted through the subject, as an image frame;
arms to hold the X-ray generator and the X-ray detector, which are kept facing each other;
a rotate-and-slide moving unit that rotates the X-ray generator and the X-ray detector around the subject horizontally, by rotating the arms around a vertical axis, and slides the rotation center of the vertical axis in the horizontal direction at the same time;
a photograph control circuit that controls the operation of the rotate-and-slide moving unit;
a storage unit that stores image frames detected sequentially by the X-ray detector along a track of a predetermined imaging plane, each of the image frames being associated with an index indicative of a detection order; and
an image processing unit for constructing a panoramic image from the image frames through image processing, wherein the image processing unit comprises:
  a pixel-value calculation routine that retrieves the image frames stored in the storage unit for each of the indices, and calculates an average value of pixel-values, indicative of the brightness of the pixel, in the retrieved image frame, then stores the average pixel-value for each of the image frames into the storage unit;
  a reference pixel-value calculation routine that calculates a reference pixel-value for all the image frames stored in the storage unit, based on at least any one of the average pixel-values stored in the storage unit, and stores the result into the storage unit;
  a pixel-value adjustment-factor calculation routine that calculates a pixel-value adjustment-factor for each of the indices, based on the inverse of the ratio of each average pixel-value stored in the storage unit by index to the reference pixel-value; and
  a panoramic image construction routine that generates an image frame of which brightness is adjusted by multiplying the pixel value of each of the pixels in each of the image frames, stored in the storage unit and being associated with the indices, by the pixel-value adjustment-factor of the corresponding index, and then constructs a panoramic image by superimposing the image frames generated for each of the indices, by a predetermined shift amount corresponding to each of the indices.

2. The X-ray photographic device according to claim 1, wherein the pixel-value adjustment-factor calculation routine comprises:
an R-value calculation subroutine that divides the reference pixel-value by the average pixel-value of each of the indices, and store an R-value indicative of the dividing result in the storage unit; and
an averaging process subroutine that calculates the average value of the R-value for a predetermined index and the R-values for a predetermined number of indices before and after the predetermined index, corrects the R-value for the predetermined index to the calculated average value and stores the result in the storage unit, and the panoramic image construction routine multiplies a pixel value of each of the pixels in each of the image frames by the corrected R-value, as the pixel-value adjustment-factor of the corresponding index.

3. The X-ray photographic device according to claim 1, wherein the pixel-value adjustment-factor calculation routine comprises:

an R-value calculation subroutine that divides the reference pixel-value by the average pixel-value of each of the indices, and store an R-value indicative of the dividing result in the storage unit; and a function estimation subroutine that estimates a hat-shaped function indicative of a hat-shaped curve line smoothly connecting the R-values in the order of the indices, by approximating the R-values for all indices to the predefined hat-shaped curve line, then corrects the R-value to the value by the hat-shaped function and stores in the storage unit, wherein the hat-shaped curve line graphically includes:
a predefined length of a first flat portion with a predetermined minimum value;
a predefined length of a second flat portion with a predetermined maximum value larger than the first flat portion;
a predefined length of a third flat portion with the same value as the first flat portion;
a first predefined continuous function connecting the first and second flat portions smoothly; and
a second predefined continuous function connecting the second and third flat portions smoothly, and the panoramic image construction routine multiplies a pixel value of each of the pixels in each of the image frames by the corrected R-value, as the pixel-value adjustment-factor of the corresponding index.

4. The X-ray photographic device according to claim 1, wherein the pixel-value adjustment-factor calculation routine comprises:

an R-value calculation subroutine that divides the reference pixel-value by the average pixel-value of each of the indices, and store the R-value indicative of the dividing result in the storage unit;

an averaging process subroutine that calculates the average value of the R-value for the predetermined index and the R-values for a predetermined number of indices before and after the predetermined index, corrects the R-value for the predetermined index to the calculated average value and stores the result in the storage unit; and a function estimation subroutine that estimates a hat-shaped function indicative of a hat-shaped curve line smoothly connecting the corrected R-values in the order of the indices, by approximating the corrected R-values for all the indices to the predefined hat-shaped curve line, then corrects the corrected R-value to the value by the hat-shaped function and stores in the storage unit, wherein the hat-shaped curve line graphically includes:
a predefined length of a first flat portion with a predetermined minimum value;
a predefined length of a second flat portion with a predetermined maximum value larger than the first flat portion;
a predefined length of a third flat portion with the same value as the first flat portion;
a first predefined continuous function connecting the first and second flat portions smoothly; and
a second predefined continuous function connecting the second and third flat portions smoothly, and the panoramic image construction routine multiplies a pixel value of each of the pixels in each of the image frames by the corrected R-value to the value of the hat-shaped function, as the pixel-value adjustment-factor of the corresponding index.

5. The X-ray photographic device according to claim 1, wherein the pixel-value calculation routine comprises:

a dark-current component subtraction subroutine that subtracts dark-current component from the detected image frame by the X-ray detector, then stores the result in the storage unit; and an average pixel-value calculation subroutine that calculates the average pixel-value of the image frame without the dark-current component.

6. The X-ray photographic device according to claim 1, wherein the reference pixel-value calculation routine retrieves the average pixel-value of the median of all indices from the storage unit, as the minimum value, then calculates the threshold value by multiplying the minimum value by a predetermined coefficient, greater than 1 and less than 2, determining the range of the indices where the average pixel-value is smaller than the threshold value, for calculating the reference pixel-value by averaging a plurality of the average pixel-values in the range of the indices determined hereinabove.

7. An image processing method, by a X-ray photographic device comprising:

a X-ray generator for irradiating a flux of X-ray to a subject;

a X-ray detector to detect the flux of X-ray that is irradiated from the X-ray generator and transmitted through the subject, as an image frame;

arms to hold the X-ray generator and the X-ray detector, which are kept facing each other;

a rotate-and-slide moving unit that rotates the X-ray generator and the X-ray detector around the subject horizontally, by rotating the arms around a vertical axis, and slides the rotation center of the vertical axis in the horizontal direction at the same time;

a photograph control circuit that controls the operation of the rotate-and-slide moving unit;

a storage unit that stores image frames detected sequentially by the X-ray detector along a track of a predetermined imaging plane, each of the image frames being associated with an index indicative of a detection order; and an image processing unit for constructing a panoramic image from the image frames through image processing, the image processing method, executed in the image processing unit, comprising:

a first step that retrieves the image frames stored in the storage unit for each of the indices, and calculates an average value of pixel-values, indicative of the brightness of the pixel, in the retrieved image frame, then stores the average pixel-value for each of the image frames into the storage unit;

a second step that calculates a reference pixel-value for all the image frames stored in the storage unit, based on at least any one of the average pixel-values stored in the storage unit, and stores the result into the storage unit;

a third step that calculates a pixel-value adjustment-factor for each of the indices, based on the inverse of the ratio of each average pixel-value stored in the storage unit by index to the reference pixel-value; and a fourth step that generates an image frame of which brightness is adjusted by multiplying the pixel value of each of the pixels in each of the image frames, stored in the storage unit and being associated with the indices, by the pixel-value adjustment-factor of the corresponding index, and then constructs a panoramic image by superimposing the image frames generated for each of the indices, by a predetermined shift amount corresponding to each of the indices.

8. The image processing method according to claim 7, wherein the third step comprises:

a division step that divides the reference pixel-value by the average pixel-value of each of the indices, and store an R-value indicative of the dividing result in the storage unit;

an averaging step that calculates an average value of the R-value for a predetermined index and the R-values for a predetermined number of indices before and after the predetermined index, corrects the R-value for the predetermined index to the calculated average value and stores the result in the storage unit; and a function estimation step that estimates a hat-shaped function indicative of a hat-shaped curve line smoothly connecting the corrected R-values in the order of the indices, by approximating the corrected R-values for all indices to the predefined hat-shaped curve line, then corrects the corrected R-value to the value by the hat-shaped function and stores the result in the storage unit, wherein the hat-shaped curve line graphically consists of:

a predefined length of a first flat portion with a predetermined minimum value;

a predefined length of a second flat portion with a predetermined maximum value larger than the first flat portion;

a predefined length of a third flat portion with the same value as the first flat portion;

a first predefined continuous function connecting the first and second flat portions smoothly; and a second predefined continuous function connecting the second and third flat portions smoothly, and the fourth step multiplies a pixel value of each of pixels in each of the image frames by the corrected R-value to the value of the hat-shaped function, as the pixel-value adjustment-factor of the corresponding index.

9. A program to execute the image processing method according to claim 7, by a computer.

* * * * *